| United States Patent [19] | [11] | 4,381,393 |
|---|---|---|
| Grisar et al. | [45] | Apr. 26, 1983 |

[54] 4-AMINOMETHYL-5-ACYL-1,3-DIHYDRO-2H-IMIDAZOL-2-ONES

[75] Inventors: J. Martin Grisar; Richard A. Schnettler; Richard C. Dage, all of Cincinnati, Ohio

[73] Assignee: Merrell Dow Pharmaceuticals Inc., Cincinnati, Ohio

[21] Appl. No.: 260,446

[22] Filed: May 4, 1981

[51] Int. Cl.³ .................. C07D 403/00; C07D 401/00; C07D 233/30

[52] U.S. Cl. .................................... 544/370; 544/365; 544/124; 544/139; 546/193; 546/210; 546/278; 548/318; 548/321

[58] Field of Search ............... 544/365, 370, 124, 139; 546/193, 210, 278; 548/318, 321

[56] References Cited

U.S. PATENT DOCUMENTS

| 2,441,933 | 7/1945 | Duschinsky | 548/321 |
| 2,514,380 | 12/1946 | Duschinsky | 548/321 |
| 3,303,199 | 2/1967 | Doebel et al. | 544/370 |
| 3,365,450 | 1/1968 | Lunsford et al. | 548/318 |

FOREIGN PATENT DOCUMENTS 3021792  1/1981  Fed. Rep. of Germany ...... 544/370

OTHER PUBLICATIONS

Duschinsky et al., J. Am. Chem. Soc., 68 2350, (1946).
Duschinsky et al., J. Am. Chem. Soc. 70, 657 (1948).
Dage et al., Fed. Proc. 39:1105 (1980) Abstract.
Boularand et al., Chimie Ther. 8, 638 (1973).

*Primary Examiner*—Mary C. Lee
*Assistant Examiner*—Sharon A. Gibson
*Attorney, Agent, or Firm*—John J. Kolano; Gary D. Street; Raymond A. McDonald

[57] ABSTRACT 1,3-Dihydro-2H-imidazol-2-ones having 5-acyl and 4-(substituted amino)methyl substituents, are useful as cardiotonics, antihypertensives and antithrombotic agents. The compounds are obtained by the reaction of an appropriate amine with a substituted 4-bromomethyl-1,3-dihydro-2H-imidazol-2-one.

10 Claims, No Drawings

4-AMINOMETHYL-5-ACYL-1,3-DIHYDRO-2H-IMIDAZOL-2-ONES

The present invention relates to imidazoles that have an acyl and an aminomethyl substituent at the 4- and 5-positions. More particularly, it relates to compounds having the following general formula:

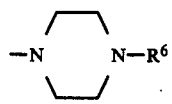

wherein R is hydrogen, lower alkyl of 1–4 C, lower alkanoyl of 2–4 C, or benzoyl; $R^1$ is lower alkyl of 1–4 C, phenyl, halophenyl, methylphenyl, methoxyphenyl, methylsulfonylphenyl, dimethylaminophenyl, dimethoxyphenyl, 3,4-methylenedioxyphenyl, 2-furyl, 2-thienyl or pyridyl; $R^2$ is hydrogen or lower alkyl of 1–4 C; and $-NR^3R^4$ is (lower alkyl)$_2$amino, 1-pyrrolidinyl, 1-piperidinyl, 4-morpholinyl,

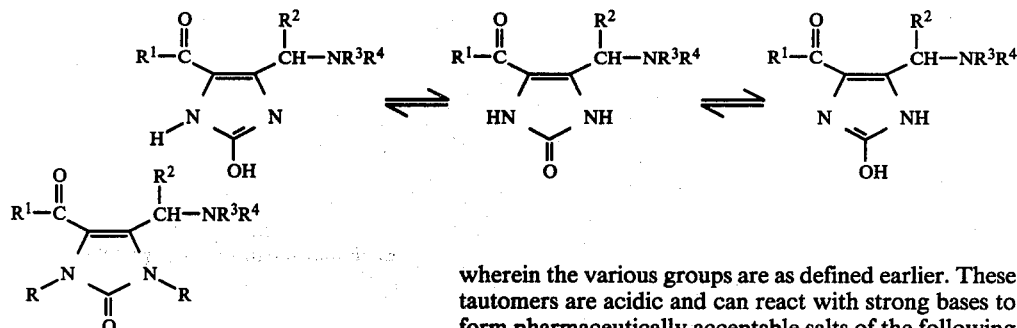

wherein $R^6$ is lower alkyl of 1–4 C, phenyl, halophenyl, methylphenyl, methoxyphenyl or trifluoromethylphenyl; and pyridinium chloride. The present invention further encompasses the pharmaceutically acceptable acid addition salts and the lower alkyl quaternary ammonium salts of the aforesaid compounds which are not already quaternized.

The lower alkyl groups referred to above contain 1 to 4 carbon atoms. Examples of such lower alkyl groups are methyl, ethyl, propyl, isopropyl and butyl. The lower alkanoyl groups referred to above contain 2 to 4 carbon atoms and can be exemplified by acetyl, propionyl and butyryl. Examples of the halophenyl groups referred to above include fluorophenyl, chlorophenyl and bromophenyl. When $-NR^3R^4$ is pyridinium chloride, the group consists of pyridine with a free valence on the nitrogen for attachment of the group to the remainder of the molecule. The pyridine nitrogen is thus quaternary so that the group must also contain an anion, preferably chloride.

Illustrative of the pharmaceutically acceptable acid addition salts of the compounds of the present invention are salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid.

Illustrative of quaternary ammonium salts are those formed with lower alkyl halides such as methyl bromide, methyl iodide, ethyl bromide and ethyl iodide.

Where R is hydrogen in the compounds of the present invention, several tautomeric forms of the compounds are possible as follows:

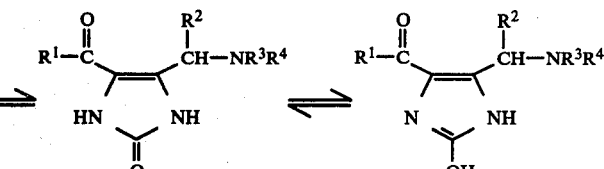

wherein the various groups are as defined earlier. These tautomers are acidic and can react with strong bases to form pharmaceutically acceptable salts of the following formulas:

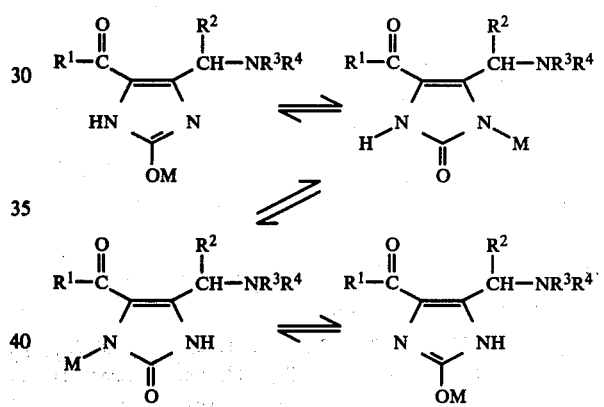

wherein the various groups are defined as above and M is a pharmaceutically acceptable alkali metal such as sodium or potassium. Throughout this disclosure, the term imidazol-2-one shall be taken to mean any of the tautomers or the tautomer salts as set forth above.

As examples of compounds of the present invention are the following:

4-Benzoyl-5-[[4-(4-chlorophenyl)-1-piperazinyl]methyl]-1,3-dihydro-2H-imidazol-2-one.

4-Propionyl-5-[[4-(2-methylphenyl)-1-piperazinyl]methyl]-1,3-dihydro-2H-imidazol-2-one.

5-[[4-(4-Fluorophenyl)-1-piperazinyl]methyl]-1,3-dihydro-4-(4-methoxybenzoyl)-2H-imidazol-2-one.

5-[[4-(3-Bromophenyl)-1-piperazinyl]methyl]-1,3-dihydro-4-(4-methoxybenzoyl)-2H-imidazol-2-one.

4-(3-Pyridylcarbonyl)-5-[[4-(2-methylphenyl)-1-piperazinyl]methyl]-1,3-dihydro-2H-imidazol-2-one.

1,3-Dihydro-5-[(4-ethyl-1-piperazinyl)methyl]-4-(4-methoxybenzoyl)-2H-imidazol-2-one.

1,3-Dihydro-4-(4-methoxybenzoyl)-5-[1-[4-(2-methylphenyl)-1-piperazinyl]ethyl]-2H-imidazol-2-one.

1,3-Dihydro-4-(4-methoxybenzoyl)-5-[(dipropylamino)methyl]-2H-imidazol-2-one.

2,3-Dihydro-4-(4-methoxybenzoyl)-N,N,N-triethyl-2-oxo-1H-imidazole-5-methanaminium bromide.

1,3-Dipropionyl-1,3-dihydro-4-(4-methoxybenzoyl)-5-[[4-(2-methylphenyl)-1-piperazinyl]methyl]-2H-imidazol-2-one.

1,3-Dibenzoyl-1,3-dihydro-4-(4-methoxybenzoyl)-5-[[4-(2-methylphenyl)-1-piperazinyl]methyl]2H-imidazol-2-one.

1,3-Dihydro-1,3-diethyl-4-(4-methoxybenzoyl)-5-[[4-(2-methylphenyl)-1-piperazinyl]methyl]-2H-imidazol-2-one.

The compounds of the present invention are prepared by the bromination of a 1,3-diacetyl imidazolone such as a compound of the formula:

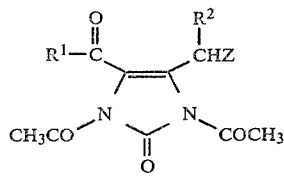

wherein Z is hydrogen to give the compound wherein Z is Br. The reaction is carried out using N-bromosuccinimide in the presence of a free radical initiator such as benzoyl peroxide in an appropriate solvent such as carbon tetrachloride. The specific diacetyl starting materials are obtained from the corresponding 1,3-unsubstituted imidazolone by acetylation with acetyl chloride or acetic anhydride and the unsubstituted imidazolones used are prepared in Belgian Pat. No. 883,856 or they can be prepared by the same general procedures described in the patent.

The bromo compounds obtained above can be treated with hydrobromic acid in acetic acid to remove one or both of the N-acetyl groups. The resulting imidazolone is then treated with the appropriate amine to give the desired compounds of the present invention. If pyridine or an appropriate tertiary amine is used in the reaction, the process gives, directly, the quarternary ammonium compounds of the present invention.

Although the present process has been described using 1,3-unsubstituted imidazolones, it is also possible to use the corresponding 1,3-diacetyl compounds or similarly substituted compounds but, when such compounds are used, the amine will also react with the acyl group to give the deacetylated imidazolone and an N-acyl amine. It is thus necessary to use an excess of the amine to allow for this reaction but this would not be a desirable process when the amine used is not readily available and inexpensive.

The compounds in which R represents lower alkanoyl or benzoyl are obtained by reaction of the compounds in which R represents hydrogen with an excess of the appropriate acid anhydride or acid chloride.

The compounds of the present invention can be used in the treatment of cardiac failure including congestive heart failure, backward heart failure, forward heart failure, left ventricular heart failure, or right ventricular heart failure or in the treatment of any other condition which requires the strengthening of heart action with a cardiotonic. In many respects, these compounds possess digitalis-like action. The compounds of the present invention can also be used in the treatment of hypertension including primary or essential hypertension, hormonally induced hypertension, renal hypertension and chemically induced hypertension. Finally, the compounds of the present invention can also be used as anti-thrombotics. They affect the coagulation of blood by preventing the aggregation of blood platelets, which play a dominant role in thrombotic conditions both in the initial event and at the occlusive stage. Arterial thrombosis, particularly in arteries supplying the heart muscle and brain, is a leading cause of death and disability.

Antihypertensive activity for the present compounds was demonstrated using groups of 12 spontaneously hypertensive rats. Blood pressure was measured by a pressure cuff occluder around the base of the tails of the rats. The blood pressure was determined in the animals, test compound was administered orally in a vehicle at a dose of 50 mg/kg and blood pressure was measured again at 1, 2, 3, 4 and 24 hours after administration of the test compound. The difference in blood pressure observed was analyzed to establish if it was statistically significant. The vehicle used in administering the test compound did not have a significant effect on blood pressure when used alone.

Cardiotonic activity for the present compounds was demonstrated by the following procedure. A Walton-Brodie strain gage arch was surgically implanted on the heart of anesthetized dogs to measure cardiac contractile force. After the vital signs of the animal were stable for 10 minutes, test compound was administered intravenously starting at a dose of 0.3 mg/kg and continuing with higher doses of 1, 3 and 10 mg/kg if no effect is observed. Active compounds, such as compounds of the present invention, which increase cardiac contractile force measured in this way exert a true positive inotropic effect, or a cardiotonic effect.

Antithrombotic activity for the present compounds is demonstrated by the following procedure. When adenosine diphosphate is added to citrated platelet rich human plasma, a typical aggregation of blood platelets occurs. Antithrombotic activity is determined by adding a test compound to the citrated platelet rich human plasma in concentrations of 3, 10, 30 and 100 μg/ml and subsequently adding adenosine diphosphate and observing the extent of inhibition of aggregation of blood platelets.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the severity of the hypertension, cardiac failure or blood clotting and the mode of administration. For oral administration the antihypertensively effective amount of compound is from about 0.1 mg/kg (milligrams per kilograms) of patient body weight per day to about 50 mg/kg of patient body weight per day and preferably from about 5 mg/kg of patient body weight per day to about 30 mg/kg of patient body weight per day.

For parenteral administration the antihypertensively effective amount of compound is from about 0.01 mg/kg of patient body weight per day up to about 50 mg/kg of patient body weight per day and preferably from about 0.1 mg/kg of patient body weight per day up to about 20.0 mg/kg of patient body weight per day. For oral or parenteral administration the cardiotonically effective amount of compound is from about 0.1 mg/kg of patient body weight per day up to about 50 mg/kg of patient body weight per day and preferably from about 0.1 mg/kg of patient body weight per day up to about 20.0 mg/kg of patient body weight per day. For oral or parenteral administration the anticoagulant effective amount of compound is from about 0.1 mg/kg of patient body weight per day up to about 100 mg/kg of patient body weight per day and preferably from about 0.1 mg/kg of patient body weight per day up to about 50 mg/kg of patient body weight per day.

For oral administration a unit dosage may contain, for example, from 10 to 100 mg of the active ingredient. For parenteral administration a unit dosage may contain, for example, from 5 to 50 mg of the active ingredient. Repetitive daily administration of the compounds may be desired and will vary with the condition of the patient and the mode of administration.

As used herein the term patient is taken to mean a warm blooded animal, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of the invention can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such as propylene glycol or polyethylene glycol can be used as liquid carriers for injectable solutions. Particularly preferred are combinations of the above carriers such as aqueous ethanol or propylene glycol-aqueous ethanol at alkaline pH.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

Following are illustrative pharmaceutical formulations which may be employed in practicing the present invention:

Preparation of a Tablet Formulation

| | | Per Tablet |
|---|---|---|
| (a) | 2,3-Dihydro-5-(4-methoxybenzoyl)-N,N,N—trimethyl-2-oxo-1H—imidazole-4-methanaminium bromide | 100 mg |
| (b) | Cornstarch | 15 mg |
| (c) | Lactose | 33.5 mg |
| (d) | Magnesium stearate | 1.5 mg |

Preparation of a Parenteral Formulation

| | | |
|---|---|---|
| (a) | 2,3-Dihydro-5-(4-methoxybenzoyl)-N,N,N—trimethyl-2-oxo-1H—imidazole-4-methanaminium bromide | 0.100 g |
| (b) | Sodium hydroxide | 0.025 g |
| (c) | Ethanol | 1.516 g |
| (d) | Propylene glycol | 8.264 g |
| (e) | Water for injection qs ad | 20.0 ml |

The following examples are set forth to illustrate the preparation of compounds employed in the present invention but should not be construed as limiting it in any way.

EXAMPLE 1

To a stirred mixture of 98.1 g (1 mole) of 1,3-dihydro-4-methyl-2H-imidazol-2-one, 266.7 g (2 moles) of anhydrous aluminum chloride and 500 ml of nitrobenzene there is added dropwise over 10 minutes, 158.6 g (1 mole) of p-fluorobenzoyl chloride. The mixture is stirred at 60°–65° C. for 6 hours, then poured onto 2 kg of ice. The precipitate which forms is separated by filtration, washed with diethyl ether and water and recrystallized from dimethylformamide to give 1,3-dihydro-4-(4-fluorobenzoyl)-5-methyl-2H-imidazol-2-one melting at about 289°–292° C.

If the above procedure is repeated using 1,3-dihydro-4-methyl-2H-imidazol-2-one and the appropriate acid chloride, the following compounds are obtained:

1,3-Dihydro-4-methyl-5-[4-(methylsulfonyl)benzoyl]-2H-imidazol-2-one.

1,3-Dihydro-4-(4-methoxybenzoyl)-5-methyl-2H-imidazol-2-one melting at about 257°–258° C. (dec.) after recrystallization from isopropanol-water.

4-Benzoyl-1,3-dihydro-5-methylimidazol-2-one melting at about 250°–254° C.

1,3-Dihydro-4-methyl-5-(2-thiophenecarbonyl)-2H-imidazol-2-one melting at about 212°–215° C. In this case, the material obtained after pouring the mixture onto ice water is extracted into ethyl acetate and the ethyl acetate solution is dried and the solvent is evaporated.

1,3-Dihydro-4-(3,4-dimethoxybenzoyl)-5-methyl-2H-imidazol-2-one melting at about 257°–259° C. after recrystallization twice from ethanol-water.

1,3-Dihydro-4-(2-furoyl)-5-methyl-2H-imidazol-2-one melting at about 214°–216° C. after recrystallization twice from methanol.

1,3-Dihydro-4-(3,4-methylenedioxybenzoyl)-5-methyl-2H-imidazol-2-one melting at about 293°–296° C. (dec).

1,3-Dihydro-5-ethyl-4-(4-methoxybenzoyl)-2H-imidazol-2-one melting at about 132° C. (dec).

1,3-Dihydro-5-methyl-4-(4-pyridinecarbonyl)-2H-imidazol-2-one melting at about 296° C. (dec).

4-Acetyl-1,3-dihydro-5-methylimidazol-2-one melting at about 314°–316° C.

EXAMPLE 2

The sodium salt of 1,3-dihydro-4-(4-methoxybenzoyl)-5-methyl-2H-imidazol-2-one is prepared from 7.0 g of 1,3-dihydro-4-(4-methoxybenzoyl)-5-methyl-2H-imidazol-2-one in 100 ml of methanol with the addition of 1.6 g of sodium methoxide. A mixture is prepared from 8.0 g of this sodium salt, 120 ml of dimethylsulfoxide, 15.2 g of powdered sodium hydroxide, and 19.5 g of methyl iodide. This mixture is stirred at room temperature for 60 minutes and then poured into 800 ml of water. The resulting mixture is then extracted with methylene chloride and the solvent is evaporated from the extract to give a solid. This is crystallized from ether to give 1,3-dihydro-4-(4-methoxybenzoyl)-1,3,5-trimethyl-2H-imidazol-2-one melting at about 109°–111° C.

EXAMPLE 3

To 2.0 g of 1,3-dihydro-4-(4-methoxybenzoyl)-5-methyl-2H-imidazol-2-one in 30 ml of dimethyl sulfoxide is added 0.29 g of sodium hydride and 1.22 g of methyl iodide. The mixture is stirred at 22° C. for 30 minutes, poured in methylene chloride, and washed with water. The methylene chloride solution is dried and the solvent is evaporated to leave an oil which is triturated with chloroform to give a solid. This solid is recrystallized from methanol to give 1,3-dihydro-(1 or 3),5-dimethyl-4-(4-methoxybenzoyl)-2H-imidazol-2-one melting at about 225°–228° C.

EXAMPLE 4

A mixture of 46.4 g of 1,3-dihydro-4-(4-methoxybenzoyl)-5-methyl-2H-imidazol-2-one and 200 ml of acetic anhydride is refluxed for 2 hours. The mixture is distilled to remove 100 ml of acetic anhydride and acetic acid; this is replaced by fresh acetic anhydride and refluxing is resumed. After a total of 4 hours of reflux, excess acetic anhydride is evaporated under reduced pressure and the resulting residue is crystallized from ethanol to give 1,3-diacetyl-1,3-dihydro-4-(4-methoxybenzoyl)-5-methyl-2H-imidazol-2-one melting at about 123°–125° C.

If the above procedure is repeated using acetic anhydride and the appropriate substituted 1,3-dihydro-2H-imidazol-2-one, the following compounds are obtained:

4-Benzoyl-1,3-diacetyl-1,3-dihydro-5-methyl-2H-imidazol-2-one melting at about 120°–122° C.

1,3-Diacetyl-1,3-dihydro-4-(4-fluorobenzoyl)-5-methyl-2H-imidazol-2-one melting at about 102°–103° C.

1,3-Diacetyl-1,3-dihydro-4-(4-dimethylaminobenzoyl)-5-methyl-2H-imidazol-2-one melting at about 183°–184° C.

1,3-Dihydro-1,3,4-triacetyl-5-methyl-2H-imidazol-2-one melting at about 73°–75° C.

1,3-Diacetyl-1,3-dihydro-4-(3,4-dimethoxybenzoyl)-5-methyl-2H-imidazol-2-one.

1,3-Diacetyl-1,3-dihydro-4-(3,4-methylenedioxybenzoyl)-5-methyl-2H-imidazol-2-one.

1,3-Diacetyl-1,3-dihydro-4-(4-methylsulfonylbenzoyl)-5-methyl-2H-imidazol-2-one.

1,3-Diacetyl-1,3-dihydro-4-(2-furoyl)-5-methyl-2H-imidazol-2-one.

1,3-Diacetyl-1,3-dihydro-4-(2-thiophenecarbonyl)-5-methyl-2H-imidazol-2-one.

1,3-Diacetyl-1,3-dihydro-5-methyl-4-(4-pyridinecarbonyl)-2H-imidazol-2-one.

1,3-Diacetyl-1,3-dihydro-5-ethyl-4-(4-methoxybenzoyl)-2H-imidazol-2-one.

EXAMPLE 5

A mixture of 55.5 g (0.176 mole) of 1,3-diacetyl-1,3-dihydro-4-(4-methoxybenzoyl)-5-methyl-2H-imidazol-2-one, 37.4 g (0.210 mole) of N-bromosuccinimide and about 100 mg of benzoyl peroxide in 500 ml of carbon tetrachloride is stirred at reflux temperature for 4 hours. The mixture is then cooled and filtered to remove the succinimide which formed. The solvent is evaporated from the filtrate and the resulting residue is crystallized from a mixture of 300 ml of ethyl acetate and 300 ml of hexane to give 5-(bromomethyl)-1,3-diacetyl-1,3-dihydro-4-(4-methoxybenzoyl)-2H-imidazol-2-one melting at about 135°–136° C.

If the above procedure is repeated using N-bromosuccinimide and the appropriate substituted 1,3-diacetyl-1,3-dihydro-2H-imidazol-2-one, the following compounds are obtained:

5-(Bromomethyl)-1,3-diacetyl-1,3-dihydro-4-(4-fluorobenzoyl)-2H-imidazol-2-one melting at about 113°–120° C.

5-(Bromomethyl)-1,3-dihydro-1,3,4-triacetyl-2H-imidazol-2-one melting at about 88°–90° C.

4-Benzoyl-5-(bromomethyl)-1,3-diacetyl-1,3-dihydro-2H-imidazol-2-one.

5-(Bromomethyl)-1,3-diacetyl-1,3-dihydro-4-(3,4-dimethoxybenzoyl)-2H-imidazol-2-one.

5-(Bromomethyl)-1,3-diacetyl-1,3-dihydro-4-(3,4-methylenedioxybenzoyl)-2H-imidazol-2-one.

5-(Bromomethyl)-1,3-diacetyl-1,3-dihydro-4-(4-methylsulfonylbenzoyl)-2H-imidazol-2-one.

5-(Bromomethyl)-1,3-diacetyl-1,3-dihydro-4-(4-dimethylaminobenzoyl)-2H-imidazol-2-one.

5-(Bromomethyl)-1,3-diacetyl-1,3-dihydro-4-(2-furoyl)-2H-imidazol-2-one.

5-(Bromomethyl)-1,3-diacetyl-1,3-dihydro-4-(2-thiophenecarbonyl)-2H-imidazol-2-one.

5-(Bromomethyl)-1,3-diacetyl-1,3-dihydro-4-(4-pyridinecarbonyl)-2H-imidazol-2-one.

5-(1-Bromoethyl)-1,3-diacetyl-1,3-dihydro-4-(4-methoxybenzoyl)-2H-imidazol-2-one.

5-(Bromomethyl)-1,3-dihydro-1,3-dimethyl-4-(4-methoxybenzoyl)-2H-imidazol-2-one.

5-(Bromomethyl)-1,3-dihydro-4-(4-methoxybenzoyl)-(1 or 3)-methyl-2H-imidazol-2-one.

EXAMPLE 6

A mixture of 50 g of 5-(bromomethyl)-1,3-diacetyl-1,3-dihydro-4-(4-methoxybenzoyl)-2H-imidazol-2-one in 75 ml of 30% hydrobromic acid in acetic acid and 150 ml of acetic acid is heated to 80° C. on a steam bath and allowed to stand for 2 hours. The mixture is then evaporated to dryness under reduced pressure and the residue is crystallized from acetic acid and then dried in vacuo at 80° C. over potassium hydroxide. This gives 5-(bromomethyl)-1,3-dihydro-4-(4-methoxybenzoyl)-2H-imidazol-2-one melting at about 205°–207° C. with decomposition.

If the above procedure is repeated using the appropriate 5-(bromomethyl)-1,3-diacetyl-1,3-dihydro-2H-imidazol-2-one, the following products are obtained:

5-(Bromomethyl)-1,3-dihydro-4-(4-fluorobenzoyl)-2H-imidazol-2-one melting at greater than 300° C. with decomposition.

4-Benzoyl-5-(bromomethyl)-1,3-dihydro-2H-imidazol-2-one.

5-(Bromomethyl)-1,3-dihydro-4-(3,4-dimethoxybenzoyl)-2H-imidazol-2-one.

5-(Bromomethyl)-1,3-dihydro-4-(3,4-methylenedioxybenzoyl)-2H-imidazol-2-one.

5-(Bromomethyl)-1,3-dihydro-4-(4-methylsulfonylbenzoyl)-2H-imidazol-2-one.

5-(Bromomethyl)-1,3-dihydro-4-(4-dimethylaminobenzoyl)-2H-imidazol-2-one.

5-(Bromomethyl)-1,3-dihydro-4-(2-furoyl)-2H-imidazol-2-one.

5-(Bromomethyl)-1,3-dihydro-4-(2-thiophenecarbonyl)-2H-imidazol-2-one.

4-Acetyl-5-(bromomethyl)-1,3-dihydro-2H-imidazol-2-one.

5-(Bromomethyl)-1,3-dihydro-4-(4-pyridinecarbonyl)-2H-imidazol-2-one.

5-(1-Bromoethyl)-1,3-dihydro-4-(4-methoxybenzoyl)-2H-imidazol-2-one.

EXAMPLE 7

A mixture of 3.1 g of 5-(bromomethyl)-1,3-dihydro-4-(4-methoxybenzoyl)-2H-imidazol-2-one, 12 ml of 30% aqueous dimethylamine and 24 ml of ethanol is stirred at 25° C. for 2 hours. The solvent is then evaporated from the mixture under reduced pressure and the resultant residue is recrystallized twice from ethanol to give 4-[(dimethylamino)methyl]-1,3-dihydro-5-(4-methoxybenzoyl)-2H-imidazol-2-one melting at about 165°-167° C. with decomposition.

If the above procedure is repeated using the appropriate amine in place of dimethylamine, the following compounds are obtained:

4-[(Diethylamino)methyl]-1,3-dihydro-5-(4-methoxybenzoyl)-2H-imidazol-2-one.

1,3-Dihydro-5-(4-methoxybenzoyl)-4-[(1-pyrrolidinyl)methyl]-2H-imidazol-2-one.

1,3-Dihydro-5-(4-methoxybenzoyl)-4-[(1-piperidinyl)methyl]-2H-imidazol-2-one.

1,3-Dihydro-5-(4-methoxybenzoyl)-4-[(4-morpholinyl)methyl]-2H-imidazol-2-one.

EXAMPLE 8

If dimethylamine is reacted with the appropriate substituted 5-(bromomethyl)-1,3-dihydro-2H-imidazol-2-one according to the procedure described in Example 7, the following compounds are obtained:

4-[(Dimethylamino)methyl]-1,3-dihydro-5-(4-fluorobenzoyl)-2H-imidazol-2-one.

5-Benzoyl-4-[(dimethylamino)methyl]-1,3-dihydro-2H-imidazol-2-one.

5-(3,4-Dimethoxybenzoyl)-4-[(dimethylamino)methyl]-1,3-dihydro-2H-imidazol-2-one.

4-[(Dimethylamino)methyl]-1,3-dihydro-5-(2-furoyl)-2H-imidazol-2-one.

5-Acetyl-4-[(dimethylamino)methyl]-1,3-dihydro-2H-imidazol-2-one.

EXAMPLE 9

To a cold solution (0° C.) of 6.0 g of 5-(bromomethyl)-1,3-diacetyl-1,3-dihydro-4-(4-methoxybenzoyl)-2H-imidazol-2-one in 50 ml of dry tetrahydrofuran is added gaseous trimethylamine over a period of 15 minutes. The mixture is stirred at 0° C. for 15 minutes and the solvent is then evaporated under reduced pressure. To the residue is added 30 ml of 30% hydrobromic acid in acetic acid and the solution is allowed to stand at 25° C. for 1 hour. The solvent is then evaporated under reduced pressure and the residue is first crystallized from water and then recrystallized from ethanol to give 2,3-dihydro-5-(4-methoxybenzoyl)-N,N,N-trimethyl-2-oxo-1H-imidazole-4-methanaminium bromide sesquihydrate melting at about 148°-150° C. with decomposition.

If the above procedure is repeated using trimethylamine and 5-(bromomethyl)-1,3-dihydro-1,3,4-triacetyl-2H-imidazol-2-one, the product obtained is 5-acetyl-2,3-dihydro-N,N,N-trimethyl-2-oxo-1H-imidazol-4-methanaminium bromide melting at about 209°-210° C. with decomposition.

EXAMPLE 10

5-(Bromomethyl)-1,3-dihydro-4-(4-methoxybenzoyl)-2H-imidazol-2-one (3.1 g) is added to 40 ml of dry pyridine and the mixture is stirred at 25° C. for 24 hours. The solvent is evaporated under reduced pressure, the residue is dissolved in 100 ml of water and the resulting solution is filtered and neutralized by addition of a weakly basic polyamine-type resin. The resin is filtered off, the filtrate is acidified with 2 N hydrochloric acid, and the mixture is then evaporated to dryness under reduced pressure. The residue is recrystallized from a mixture of 2-propanol and water to give 1-[[2,3-dihydro-5-(4-methoxybenzoyl)-2-oxo-1H-imidazol-4-yl]methyl]pyridinium chloride melting at about 239°-240° C. with decomposition.

EXAMPLE 11

A mixture of 6.2 g of 4-(bromomethyl)-1,3-dihydro-5-(4-methoxybenzoyl)-2H-imidazol-2-one, 5.0 g of 1-(2-methylphenyl)piperazine dihydrochloride and 5.4 g of potassium carbonate in 100 ml of ethanol is stirred at room temperature for 24 hours. Water is added to the reaction mixture and the precipitate which forms is separated by filtration. The solid is then suspended in 2-propanol, 1 equivalent of hydrochloric acid is added, and the resulting solid is separated and recrystallized from 2-propanol/water to give 1,3-dihydro-4-(4-methoxybenzoyl)-5-[[4-(2-methylphenyl)-1-piperazinyl]methyl]-2H-imidazol-2-one hydrochloride melting at about 223°-225° C. with decomposition.

The free base of this compound has the following structural formula:

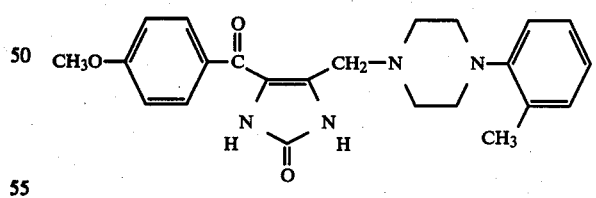

EXAMPLE 12

If the procedure of Example 11 is repeated using the appropriate substituted piperazine in place of the 1-(2-methylphenyl)piperazine and the procedure of Example 11 is repeated, the following compounds are obtained:

1,3-Dihydro-4-(4-methoxybenzoyl)-5-[(4-methyl-1-piperazinyl)methyl]-2H-imidazol-2-one hydrochloride.

5-[[4-(4-Chlorophenyl)-1-piperazinyl]methyl]-1,3-dihydro-4-(4-methoxybenzoyl)-2H-imidazol-2-one hydrochloride.

1,3-Dihydro-4-(4-methoxybenzoyl)-5-[[4-(2-methoxyphenyl)-1-piperazinyl]methyl]-2H-imidazol-2-one hydrochloride.

1,3-Dihydro-4-(4-methoxybenzoyl)-5-[[4-(3-trifluoromethylphenyl)-1-piperazinyl]methyl]-2H-imidazol-2-one hydrochloride.

EXAMPLE 13

If 1-(2-methylphenyl)piperazine dihydrochloride is reacted with the appropriate 5-substituted 4-(bromoalkyl)-1,3-dihydro-2H-imidazol-2-one according to the procedure described in Example 11, the following compounds are obtained:

1,3-dihydro-4-(4-fluorobenzoyl)-5-[[4-(2-methylphenyl)-1-piperazinyl]methyl]-2H-imidazol-2-one hydrochloride.

4-Benzoyl-1,3-dihydro-5-[[4-(2-methylphenyl)-1-piperazinyl]methyl]-2H-imidazol-2-one hydrochloride.

1,3-Dihydro-4-(3,4-dimethoxybenzoyl)-5-[[4-(2-methylphenyl)-1-piperazinyl]methyl]-2H-imidazol-2-one hydrochloride.

1,3-Dihydro-4-(3,4-methylenedioxybenzoyl)-5-[[4-(2-methylphenyl)-1-piperazinyl]methyl]-2H-imidazol-2-one hydrochloride.

1,3-Dihydro-5-[[4-(2-methylphenyl)-1-piperazinyl]methyl]-4-(4-methylsulfonylbenzoyl)-2H-imidazol-2-one hydrochloride.

1,3-Dihydro-4-(4-dimethylaminobenzoyl)-5-[[4-(2-methylphenyl)-1-piperazinyl]methyl]-2H-imidazol-2-one hydrochloride.

1,3-Dihydro-4-(2-furoyl)-5-[[4-(2-methylphenyl)-1-piperazinyl]methyl]-2H-imidazol-2-one hydrochloride.

1,3-Dihydro-5-[[4-(2-methylphenyl)-1-piperazinyl]methyl]-4-(2-thiophenecarbonyl)-2H-imidazol-2-one hydrochloride.

1,3-Dihydro-5-[[4-(2-methylphenyl)-1-piperazinyl]methyl]-4-(4-pyridinecarbonyl)-2H-imidazol-2-one hydrochloride.

1,3-Dihydro-4-(4-methoxybenzoyl)-5-[1-[4-(2-methylphenyl)-1-piperazinyl]ethyl]-2H-imidazol-2-one hydrochloride.

4-Acetyl-1,3-dihydro-5-[[4-(2-methylphenyl)-1-piperazinyl]methyl]-2H-imidazol-2-one hydrochloride.

1,3-Dihydro-1,3-dimethyl-4-(4-methoxybenzoyl)-5-[[4-(2-methylphenyl)-1-piperazinyl]methyl]-2H-imidazol-2-one hydrochloride.

EXAMPLE 14

1,3-Dihydro-4-(4-methoxybenzoyl)-5-[[4-(2-methylphenyl)-1-piperazinyl]methyl]-2H-imidazol-2-one hydrochloride is converted to the free base by standard procedures and then treated with a large excess of refluxing acetic anhydride for 4 hours. Excess acetic anhydride is evaporated under reduced pressure and the resultant residue is recrystallized twice from a mixture of ethyl acetate and ethanol to give 1,3-diacetyl-1,3-dihydro-4-(4-methoxybenzoyl)-5-[[4-(2-methylphenyl)-1-piperazinyl]methyl]-2H-imidazol-2-one.

What is claimed is:

1. A compound of the formula

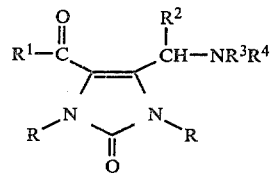

wherein R is hydrogen, lower alkyl of 1–4 C, lower alkanoyl of 2–4 C, or benzoyl; $R^1$ is lower alkyl of 1–4 C, phenyl, halophenyl, methylphenyl, methoxyphenyl, methylsulfonylphenyl, dimethylaminophenyl, dimethoxyphenyl, 3,4-methylenedioxyphenyl, 2-furyl, 2-thienyl or pyridyl; $R^2$ is hydrogen or lower alkyl of 1–4 C; and $-NR^3R^4$ is (lower alkyl)$_2$amino, 1-pyrrolidinyl, 1-piperidinyl, 4-morpholinyl,

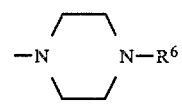

wherein $R^6$ is lower alkyl of 1–4 C, phenyl, halophenyl, methylphenyl, methoxyphenyl or trifluoromethylphenyl; and the pharmaceutically acceptable acid addition salts and the lower alkyl quarternary ammonium salts of the aforesaid compounds.

2. A compound according to claim 1 which has the formula

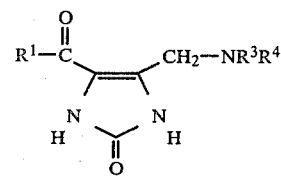

wherein $R^1$ is lower alkyl of 1–4 C, phenyl, halophenyl, methylphenyl, methoxyphenyl, methylsulfonylphenyl, dimethylaminophenyl, dimethoxyphenyl, 3,4-methylenedioxyphenyl, 2-furyl, 2-thienyl or pyridyl; and $-NR^3R^4$ is (lower alkyl)$_2$amino, 1-pyrrolidinyl, 1-piperidinyl, 4-morpholinyl,

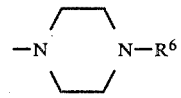

wherein $R^6$ is lower alkyl of 1–4 C, phenyl, halophenyl, methylphenyl, methoxyphenyl or trifluoromethylphenyl.

3. A compound according to claim 1 which has the formula

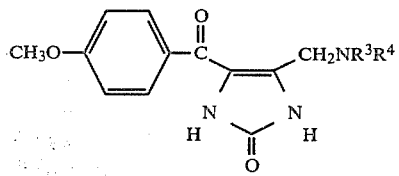

wherein $-NR^3R^4$ is (lower alkyl)$_2$amino, 1-pyrrolidinyl, 1-piperidinyl, 4-morpholinyl,

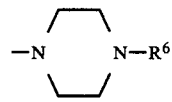

wherein $R^6$ is lower alkyl of 1–4 C, phenyl, halophenyl, methylphenyl, methoxyphenyl or trifluoromethylphenyl.

4. A compound according to claim 1 which has the formula

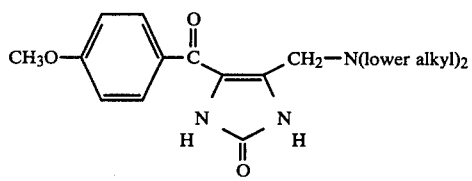

5. A compound according to claim 1 which is 4-[(dimethylamino)methyl]-1,3-dihydro-5-(4-methoxybenzoyl)-2H-imidazol-2-one.

6. A compound according to claim 1 which is 2,3-dihydro-5-(4-methoxybenzoyl)-N,N,N-trimethyl-2-oxo-1H-imidazole-4-methanaminium bromide.

7. A compound according to claim 1 which is 5-acetyl-2,3-dihydro-N,N,N-trimethyl-2-oxo-1H-imidazole-4-methanaminium bromide.

8. A compound according to claim 1 which has the formula

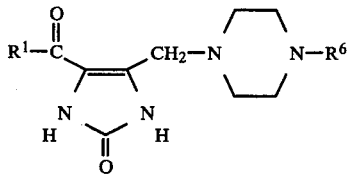

wherein $R^1$ is lower alkyl of 1–4 C, phenyl, halophenyl, methylphenyl, methoxyphenyl, methylsulfonylphenyl, dimethylaminophenyl, dimethoxyphenyl, 3,4-methylenedioxyphenyl, 2-furyl, 2-thienyl or pyridyl; and $R^6$ is lower alkyl of 1–4 C, phenyl, halophenyl, methylphenyl or trifluoromethylphenyl.

9. A compound according to claim 1 which has the formula

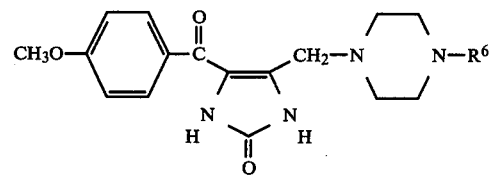

wherein $R^6$ is lower alkyl of 1–4 C, phenyl, halophenyl, methylphenyl, methoxyphenyl or trifluoromethylphenyl.

10. A compound according to claim 1 which is 1,3-dihydro-4-(4-methoxybenzoyl)-5-[[4-(2-methylphenyl)-1-piperazinyl]methyl]-2H-imidazol-2-one.

* * * * *